United States Patent
Giri et al.

(10) Patent No.: US 10,332,619 B2
(45) Date of Patent: Jun. 25, 2019

(54) METHODS AND APPARATUS FOR IN SILICO PREDICTION OF CHEMICAL REACTIONS

(71) Applicant: Samsung Electronics Co., Ltd., Suwon-si, Gyeonggi-do (KR)

(72) Inventors: Varun Giri, Bangalore (IN); Venkata Tadi Siva Kumar, Bangalore (IN); Anirban Bhaduri, Bangalore (IN); Kyusang Lee, Ulsan (KR); Saswati Dana, Bangalore (IN); Taeyong Kim, Daejeon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 284 days.

(21) Appl. No.: 14/854,222

(22) Filed: Sep. 15, 2015

(65) Prior Publication Data
US 2016/0103979 A1    Apr. 14, 2016

(30) Foreign Application Priority Data

Oct. 13, 2014   (IN) .......................... 5126/CHE/2014
Feb. 9, 2015    (KR) ........................ 10-2015-0019728

(51) Int. Cl.
   *G01N 33/48*   (2006.01)
   *G01N 33/50*   (2006.01)
   *G16C 20/10*   (2019.01)

(52) U.S. Cl.
   CPC ................................... *G16C 20/10* (2019.02)

(58) Field of Classification Search
   None
   See application file for complete search history.

(56) References Cited

U.S. PATENT DOCUMENTS

| 8,401,797 B2 | 3/2013 | Hlavacek et al. |
| 2003/0229477 A1 | 12/2003 | Schurer et al. |
| 2005/0119837 A1 | 6/2005 | Prakash et al. |
| 2010/0250218 A1 | 9/2010 | Ekins et al. |

FOREIGN PATENT DOCUMENTS

| JP | 2007-534318 A | 11/2007 |
| WO | WO 2005/083618 A2 * | 9/2005 |

OTHER PUBLICATIONS

Cornilescu et al. Protein backbone angle restraints from searching a database for chemical shift and sequence homology. Journal of Biomolecular NMR, vol. 13, pp. 289-302. (Year: 1999).*
Yim et al. "Metabolic engineering of *Escherichia coli* for direct production of 1,4-butanediol," *Nature Chemical Biology*, vol. 7 (2011).
www.eyesopen.com "Toolkit Development Platform" (2013).
www.chemaxon.com/products/reactor, "Reactor, a high performance virtual synthesis engine" (1998).

* cited by examiner

*Primary Examiner* — Russell S Negin
(74) *Attorney, Agent, or Firm* — Leydig, Voit & Mayer, Ltd.

(57) ABSTRACT

Provided are a method and apparatus for designing and processing a rule pipeline for in silico prediction of chemical reactions. The method includes designing a rule pipeline from at least one rule for chemical conversion and processing at least one input molecule by using the designed rule pipeline to predict a chemical reaction based on a processing result of the processing.

18 Claims, 14 Drawing Sheets

METHODS AND APPARATUS FOR IN SILICO PREDICTION OF CHEMICAL REACTIONS

RELATED APPLICATIONS

This application claims the benefits of Indian Patent Application No. 5126/CHE/2014, filed on Oct. 13, 2014, and Korean Patent Application No. 10-2015-0019728, filed on Feb. 9, 2015, in the Korean Intellectual Property Office, the disclosures of which are incorporated herein in their entirety by reference.

BACKGROUND

1. Field

The present disclosure relates to computational chemistry, and more particularly to in silico prediction of chemical reactions by designing and processing reaction rule pipelines.

2. Description of the Related Art

Identification of novel pathways for synthesis or degradation of molecules remains a challenge in synthetic chemistry, drug discovery, and biotechnology. To this end, assessment of all potential precursors and associated chemical transformations from a starting molecule leading to a target molecule is required. However, exhaustive screening of all possible chemical transformations is experimentally intractable, and thus, computational chemistry for investigating the behavior of atoms and molecules through computer simulations has been studied.

Identification of novel chemical pathways regarding chemical reactions using a computer is called in silico identification and requires two components: a reaction rule library and a knowledge based reaction prediction system.

The reaction rule library may include rules for chemical conversion. A rule for chemical conversion may represent a chemical transformation and may include necessary information that describes the conversion of a reactant into a product based on a chemical transformation. These rules are either derived from a set of known chemical reactions or may be constructed from basic chemical principles.

A knowledge-based reaction prediction system applies rules from the reaction rule library on an input and predicts a set of products or precursors. To generate multi-step pathways, the rules may be iteratively applied on predicted products and/or precursors. In order to select an experimental tractable synthetic pathway, appropriate start and end molecules may be obtained via the knowledge-based reaction prediction system.

Generally, the knowledge-based reaction prediction system involves a sub-graph alignment to identify a functional group pattern on input molecules, which is computationally intensive. Various physio-chemical properties may also be computed to ascertain the possibility of an input molecule undergoing a reaction transformation. These computations are performed once for each rule on each input and account for most of the computational time in a reaction prediction process. Thus, in the case of a large set of reaction rules and iterative computations, the system may take a long time to predict pathways. Also, the computational intensiveness increases exponentially with each iteration, which restricts higher order simulations.

SUMMARY

Provided are methods and apparatuses for in silico prediction, in which chemical reaction rule pipelines are designed and processed to predict a chemical reaction.

Provided are computer readable recording media for executing the methods described above.

Additional aspects will be set forth in part in the description which follows and, in part, will be apparent from the description, or may be learned by practice of the presented exemplary embodiments.

According to an aspect of an exemplary embodiment, a method for in silico prediction of chemical reactions, includes: designing a rule pipeline; processing at least one input molecule using the designed rule pipeline; and predicting a chemical reaction based on the at least one processed input molecule, wherein the designed rule pipeline is an arrangement of a plurality of phases including at least one rule for chemical conversion.

The designing of the rule pipeline may include: processing the at least one rule for chemical conversion based on at least one physiochemical attribute defined in a schema; grouping the processed at least one rule for chemical conversion into at least one group; and designing the rule pipeline for each of the at least one group.

The designing of the rule pipeline for each of the at least one group may include: processing the plurality of rules of the one group to extract rules; and arranging the extracted rules, wherein the arranging of the at least one extracted rule includes arranging the at least one phase including the at least one extracted rule, and in the arranging of the plurality of phases, the plurality of phases are arranged such that at least one output of a current phase is fed as at least one input of a subsequent phase.

The designing of the rule pipeline for each of the at least one group may further include connecting a plurality of extracted rules to one another via a logical operator.

Each of the at least one extracted rule may be one of a validation rule and a transformation rule.

In the designing of the rule pipeline, each phase may be designed to perform one of validation and transformation based on the rule included in the each phase.

In the designing of the rule pipeline, a lead phase arranged as a lead phase of the rule pipeline may receive the at least one input molecule while a terminal phase arranged as a last phase generates the at least one processed molecule as an output.

The designing of the rule pipeline may include designing at least one phase for receiving, generating, or modifying associated information, and the associated information may include an atom of a molecule that is received as an input by a current phase and is processed in a previous phase, an atom of at least one molecule that is eligible for processing in the current phase, a result of at least one computation performed previously, at least one user parameter, and at least one user configuration, wherein the generating or modifying of the associated information is performed by at least one of adding, deleting, and overwriting the associated information.

In the designing of the rule pipeline, the at least one rule pipeline may be designed such that one of validation or transformation of the input molecule is performed based on the associated information in each of the at least one phase.

In the designing of the rule pipeline, a phase may be designed to omit processing of at least atom with respect to at least one molecule received as an input by at least one phase, and information about the at least one atom for which the processing is omitted is included in the associated information.

The designing of the rule pipeline may include designing at least one phase as an optional phase, wherein if the optional phase fails to produce an output from a received input, the optional phase generates the received input as an output with no modification.

The designing of the rule pipeline may include designing at least one phase as a metaphase including at least one rule pipeline, and the metaphase may include at least one rule pipeline, and if the metaphase includes at least two rule pipelines, the rule pipelines may be arranged in parallel.

In the designing of the rule pipeline, the metaphase may be designed such that the at least one input molecule is validated or transformed.

In the designing of the rule pipeline, the designing of the rule pipeline may be performed via a directed graph, wherein the at least one phase receives at least one input from at least one previous phase and forwards the at least one output to at least one subsequent phase.

The designing of the rule pipeline may include grouping the plurality of phases into at least one stage, wherein while a terminal phase arranged as a last phase generates the at least one processed molecule as an output, a lead phase arranged as a lead phase receives the at least one input molecule.

In the designing of the rule pipeline, the at least one rule pipeline may be designed such that a plurality of rules included in a current phase applies independently or cumulatively to at least one input received by the current phase from a plurality of previous phases.

The processing of the at least one input molecule via the rule pipeline may include: receiving at least one molecule; and sequentially processing the at least one input molecule according to at least one phase of the rule pipeline, wherein in the sequentially processing, at least one output of at least one phase from among the at least one phase is fed as an input of a subsequent phase.

The predicting of a chemical reaction based on the at least one processed molecule may include selecting one of the at least one phase to predict at least one chemical reaction based on the selected phase.

According to an aspect of another exemplary embodiment, an in silico prediction apparatus, includes: a memory; and at least one processor operatively coupled to the memory, wherein the at least one processor includes: a rule pipeline designing unit configured to design a rule pipeline; an input receiving unit configured to receive at least one molecule to be processed; a rule pipeline processing unit configured to process the at least one molecule according to at least one phase of the rule pipeline; and a chemical reaction predicting unit configured to predict at least one chemical reaction based on at least one output according to processing based on the rule pipeline.

According to an aspect of another exemplary embodiment, a non-transitory computer readable recording medium having embodied thereon a program for executing the method described above is included.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
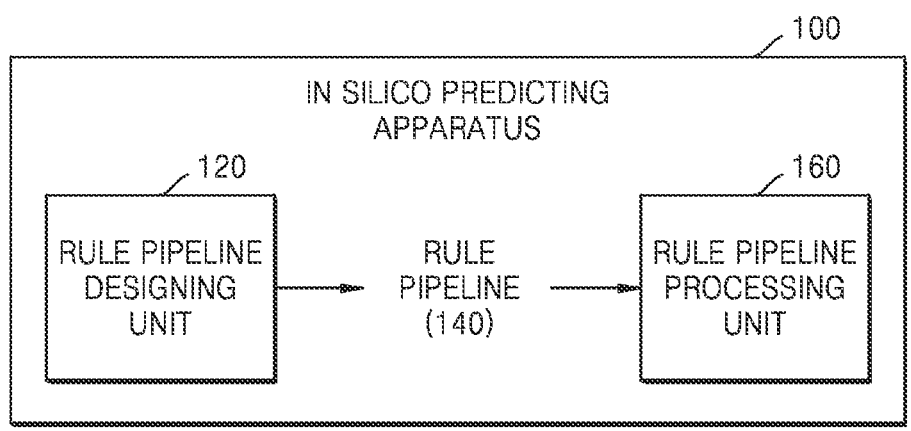
FIG. 1 illustrates an in silico predicting apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

The advantages and features of the inventive concept and methods of achieving the advantages and features will be described more fully with reference to the accompanying drawings, in which exemplary embodiments of the inventive concept are shown. The inventive concept may, however, be embodied in many different forms and should not be construed as being limited to the embodiments set forth herein; rather these embodiments are provided so that this disclosure will be thorough and complete, and will fully convey the concept of the inventive concept to one of ordinary skill in the art.

The terms used in this specification are those general terms currently widely used in the art in consideration of functions in regard to the inventive concept, but the terms may vary according to the intention of those of ordinary skill in the art, precedents, or new technology in the art. Also, specified terms may be selected by the applicant, and in this case, the detailed meaning thereof will be described in the detailed description of the inventive concept. Thus, the terms used in the specification should be understood not as simple names but based on the meaning of the terms and the overall description of the inventive concept.

Throughout the specification, it will also be understood that when a component "includes" an element, unless there is another opposite description thereto, it should be understood that the component does not exclude another element but may further include another element. In addition, terms such as " . . . unit" used in the specification refers to a hardware component such as software or hardware component such as FPGA or ASIC, and a " . . . unit" performs certain functions. However, a " . . . unit" is not limited to software or hardware. A " . . . unit" may be configured in an addressable storage medium or to reproduce one or more processors. Thus, for example, a " . . . unit" includes components such as software components, object-oriented software components, class components, task components, processes, functions, attributes, procedures, subroutines, segments of programs codes, drivers, firmware, microcodes, circuits, data, databases, data structures, tables, arrays, and variables. Functions provided in the components and the " . . . units" may be combined with a smaller number of components and " . . . units" or separated from additional components and " . . . units."

The present embodiments have been described with reference to specific example embodiments; it will be evident that various modifications and changes may be made to these embodiments without departing from the broader spirit and scope of the various embodiments. Furthermore, the various devices, modules, and the like described herein may be enabled and operated using hardware circuitry, for example, complementary metal oxide semiconductor based logic circuitry, firmware, software and/or any combination of hardware, firmware, and/or software embodied in a machine readable medium.

Hereinafter, an element used in the singular may denote the element in the plural although there is no particular qualifier therefor. For example, a "molecule" or "input molecule" input to a rule pipeline may include one or more molecules or one or more input molecules, and a "molecule" may include at least one atom.

The features disclosed in the embodiments and drawings of the present specification are examples of embodiments of the inventive concept, and thus it should be understood that there are alternative equivalents or variation examples that can replace the embodiments at the point of the filing of the present application.

FIG. 1 illustrates an in silico predicting apparatus 100 according to an exemplary embodiment.

The in silico predicting apparatus 100 includes a rule pipeline designing unit 120, a rule pipeline 140, and a rule pipeline processing unit 160 for in silico prediction of a chemical reaction. The rule pipeline 140 may be a (chemical) reaction rule pipeline.

The rule pipeline designing unit 120 may design the rule pipeline 140 from a set of rules for chemical conversion. The rule pipeline processing unit 160 may process the designed rule pipeline 140 to predict a chemical reaction.

The rule pipeline 140 according to an exemplary embodiment may include a set of processing elements, e.g., software units or modules. The processing elements are sequentially arranged such that an output of a one element is an input of a next element. Also, the rule pipeline 140, in one embodiment, refers to a linear and directional flow of image processing and may include a phase alignment flow in a directed graph.

The rule pipeline 140 may be an arrangement of instructions to process data regarding one or more molecules for a chemical conversion. The instructions may be extracted from a set of rules for a chemical conversion.

The rule pipeline designing unit 120 may process a set of rules for a chemical conversion and group the processed rules to design a rule pipeline of each group. The rule pipeline designing unit 120 according to an exemplary embodiment may design the rule pipeline 140 based on a schema.

The schema may be used to form rule pipelines from a set of rules for chemical conversion. The rule pipeline designing unit 120 may provide instructions to process and group sets of rules for chemical conversion based on physio-chemical attributes defined in the schema.

The physio-chemical attributes defined in the schema include, without limitation, atoms participating in the transformation (e.g., reactant product or functional group), attributes relating to spontaneous transformation following a reaction conversion, and environmental conditions such as pH, temperature, or the like.

The schema further provides instructions for splitting, merging and/or creating rules based on the rules grouped together. The rules thus obtained are called 'extracted rules'. Steps common to multiple rules in a group are condensed into a singular rule.

The schema may provide a blueprint of the rule pipeline 140. The extracted rules may be arranged according to the blueprint.

The rule pipeline processing unit 160 may predict a chemical reaction regarding an input molecule by processing the rule pipeline 140. The rule pipeline processing unit 160 according to an exemplary embodiment may receive an input molecule and associated information, and may process the received molecule according to each phase of the rule pipeline 140 and output the same. Although the in silico predicting apparatus 100 may use an input molecule and associated information when the rule pipeline 140 is processed, the associated information is not essentially necessary. In other words, the associated information may be selectively received or transmitted and used.

The rule pipeline processing unit 160 may predict a chemical reaction based on the processed input molecule.

Figure 2:
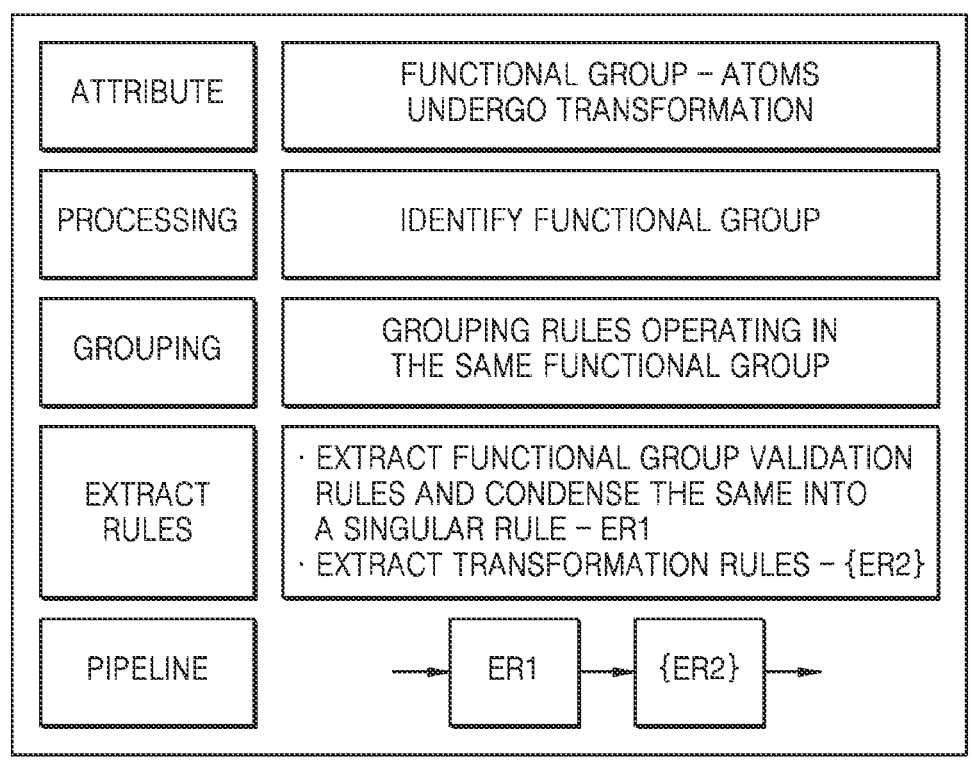
FIG. 2 illustrates a schema for a rule pipeline according to an exemplary embodiment.

FIG. 2 illustrates a schema for a rule pipeline according to an exemplary embodiment.

FIG. 2 illustrates an example where the schema uses a functional group as attributes for grouping given rules. Atoms undergo transformation during reaction transformation represented by the rules. All rules operating in the same functional group may be grouped together.

Each rule in a group is split into a functional group validation rule and a transformation rule. All validation rules are condensed together into a single validation rule ER1, and transformation rules are put together as set of rules, {ER2}. The schema may finally provide a structure of a rule pipeline in which the extracted rules are arranged.

Figure 3A:
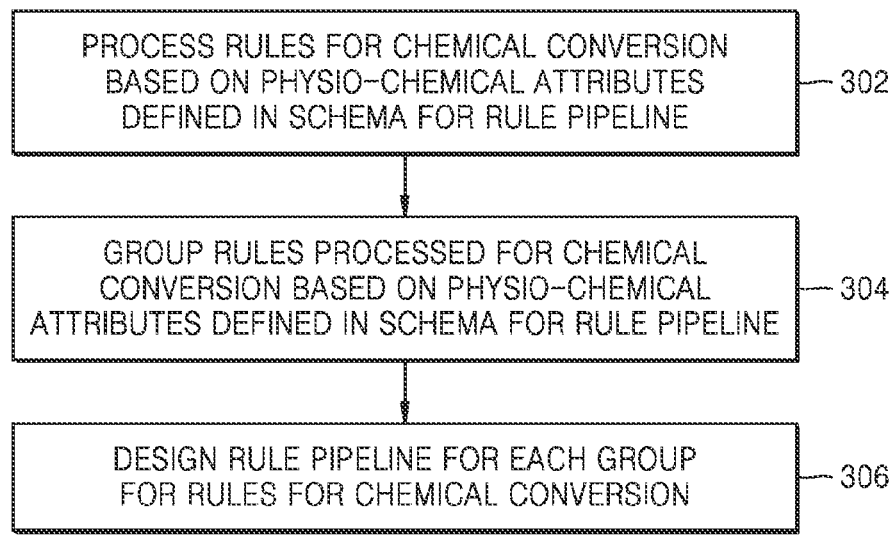
FIG. 3A is a flowchart illustrating a method of designing a rule pipeline by using an in silico predicting apparatus, according to an exemplary embodiment.

FIG. 3A is a flowchart illustrating a method of designing a rule pipeline using an in silico predicting apparatus, according to an exemplary embodiment. Each operation of the method of FIG. 3A may be performed using the rule pipeline designing unit 120.

One or more rules for chemical conversion whereby a group is formed based on physiochemical attributes defined in a schema with respect to a rule pipeline may be processed in operation 302. In this operation, each input rule may be evaluated based on the attributes defined in the schema for rule pipelines.

The processed rules for chemical conversion are then grouped based on the physiochemical attributes defined in the schema for the rule pipelines in operation 304. For example, all of the rules for chemical conversion acting on the same functional group may be grouped together.

Each individual group identified in operation 304 may be further processed to design a rule pipeline in operation 306.

Figure 3B:
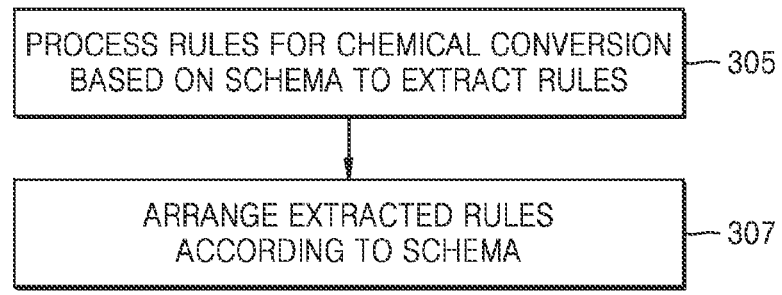
FIG. 3B is a flowchart illustrating a method of designing a rule pipeline for a group of rules, by using an in silico predicting apparatus according to an exemplary embodiment.

FIG. 3B is a flowchart illustrating a method of designing a rule pipeline based on a set of processed rules, using an in silico predicting apparatus, according to an exemplary embodiment. Each operation of the method of FIG. 3B may be performed using the rule pipeline designing unit 120.

As a first operation of designing the rule pipeline, a rule for chemical conversion may be processed to extract rules based on the schema for the rule pipelines in operation 305. Each of the extracted rules may be either a validation rule or a transformation rule.

In operation 307, the rules extracted in operation 305 may be arranged.

The rule pipeline according to an exemplary embodiment may be designed such that a lead phase receives a user input (i.e., a molecule), while a terminal phase arranged as a last phase provides processed molecules as an output. The molecules according to an exemplary embodiment may be represented using one of standard molecular representations such as Simplified Molecular Input Line Entry System (SMILES), Molecular Design Limited (MDL) MOL, and Chemical Markup Language (CML). The atoms of the molecules may be represented as native elements or derived atom types.

Apart from the input of molecules, the lead phase may optionally receive associated information. Also, the remaining phases of the rule pipeline may be arranged sequentially such that an output of a phase and the optional associated information are fed as an input to a subsequent phase. The sequential arrangement of phases is designed so as to retain the natural flow of the chemical conversion.

Figure 4:
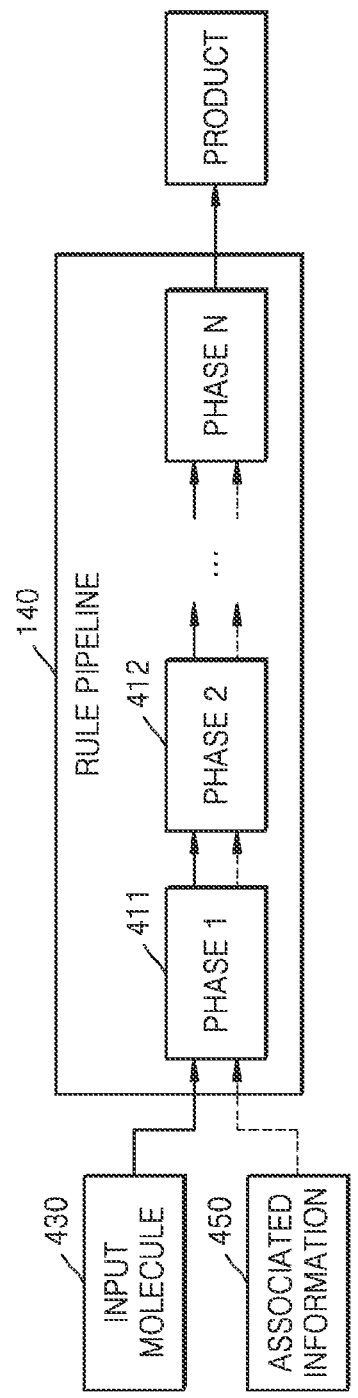
FIG. 4 illustrates a rule pipeline according to an embodiment.

FIG. 4 illustrates a rule pipeline 140 according to an embodiment.

Referring to FIG. 4, a solid arrow denotes the flow of molecules, and a dotted arrow denotes the flow of associated information. The rule pipeline designing unit 120 may design the rule pipeline 140 of FIG. 4 by arranging a plurality of phases.

Each phase of the rule pipeline 140 may include at least one extracted rule, and may be designed to perform either validation or transformation using the extracted rule included in the phase or using the extracted rules and associated information at the same time. Each rule in the phase may be processed independently to derive an output.

In a phase designed for validation, according to an exemplary embodiment, an input molecule 430 received as an input is processed as per the rules in the phase, optionally using associated information 450. After successful validation, the phase designed for validation may forward the input molecule 430 with no modification.

In a phase designed for transformation, according to an exemplary embodiment, the input molecule 430 received as an input may be processed as per the rules in the phase, optionally using associated information 450. The phase designed for transformation may forward the transformed molecule as an output.

The associated information 450 received by a phase according to an exemplary embodiment may include, without limitation, atoms of molecules that are processed in a previous phase and received as an input, atoms that may be processed in the phase, a result of previously performed computation, a user parameter, user environment setting information, or a combination thereof.

The associated information 450 may be used to optimize an operation of the rule pipeline 140 for input molecules. For example, a user may provide environmental parameters, such as pH or temperature, and these environmental parameters may be used in the rule pipeline 140 to process the input molecules.

According to an exemplary embodiment, application of the rule pipeline 140 may be restricted to a sub-set of atoms of the input molecules. For example, for a biomolecule containing coenzyme-A (CoA) moiety, when it is desirable that the CoA moiety remains intact while the remaining atoms are allowed to undergo a transformation, the restriction may be provided by specifying, based on the associated information 450, specific atoms of the input molecule 430 that are to be processed in the rule pipeline 140.

According to another exemplary embodiment, a phase of the rule pipeline 140 may be designed either to create associated information or to modify the associated information by adding or deleting or overwriting information or by combining these. Accordingly, when the in silico predicting apparatus 100 processes the rule pipeline 140, computations already performed by previous phases may be used by the current phase, thereby avoiding redundant computations.

According to another exemplary embodiment, the rule pipeline 140 may be designed such that atoms of the input molecule 430 that are marked in a previous phase are processed. Information about these atoms may be passed along the input molecule 430 as the associated information 450. For example, a position of a predetermined functional group that is computed while validating the presence of the functional group in a validation operation may be used to apply transformations in a subsequent operation.

According to another exemplary embodiment, the rule pipeline 140 may be designed such that a phase therein is not allowed to process atoms of the input molecules 430 processed in a previous phase, and information about the atoms of the input molecules 430 that are not processed may be received as the associated information 450 from the previous phase.

According to another exemplary embodiment, the rule pipeline 140 may be designed by connecting extracted rules of a phase via logical operators. When a validation rule is applied, a logical value such as true or false may be output, and when a transformation rule is applied, a transformed molecule may be produced as an output. It is deemed as true if the transformation rule produces an output and false otherwise.

In a phase, two or more rules may be connected via logical operators. For example, if a validation rule and a transformation rule in the phase are linked with an AND logic, an input may be validated as per the validation rule and may be transformed as per the transformation rule. The net output may be produced from the rules by a logical operation, and may be forwarded to another phase.

According to another exemplary embodiment, the rule pipeline 140 may be designed to include an optional phase. If the optional phase fails to produce an output from a received input, the received input may remain unchanged and be forwarded with no modification. For example, if all rules in a phase including a plurality of transformation rules are designated as optional, and the phase fails to produce a transformation product, an input molecule of the phase may be forwarded as an output of the phase with no modification.

Figure 5:
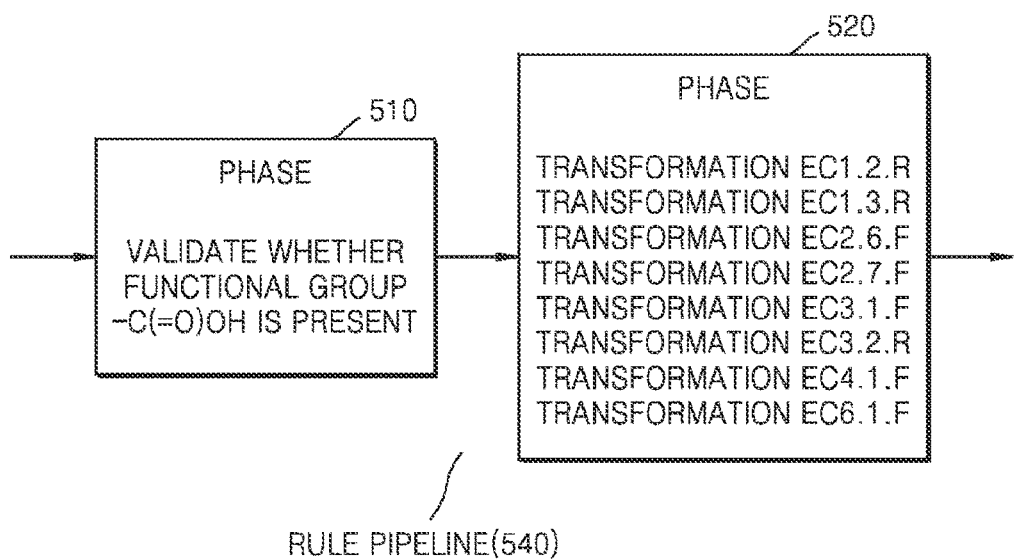
FIG. 5 illustrates a rule pipeline according to an embodiment.

The rule pipeline 540 of FIG. 5 includes two phases 510 and 520. The rule pipeline 540 may be constructed by the rule pipeline designing unit 120 of the in silico predicting apparatus 100 based on rules listed in Table 1 (below) and the schema described with reference to FIG. 2.

The phase 510 may receive an input molecule and include a validation rule which identifies and validates the presence of a functional group, for example, a carboxyl group (—COOH), in the input molecule. The phase 510 may forward the input molecule to the phase 520 after successful validation.

The phase 510 may transmit a position of an identified functional group to the phase 520 as associated information, and the phase 520 may apply a transformation rule by using the received information.

This phase 520 may include a set of transformation rules. Each of the transformation rules is applied on the input molecule. If a predetermined functional group is not present in the input molecule, the in silico predicting apparatus 100 may design a rule pipeline such that all rules applied to the above functional group are excluded from processing of the entire pipeline.

Figure 6:
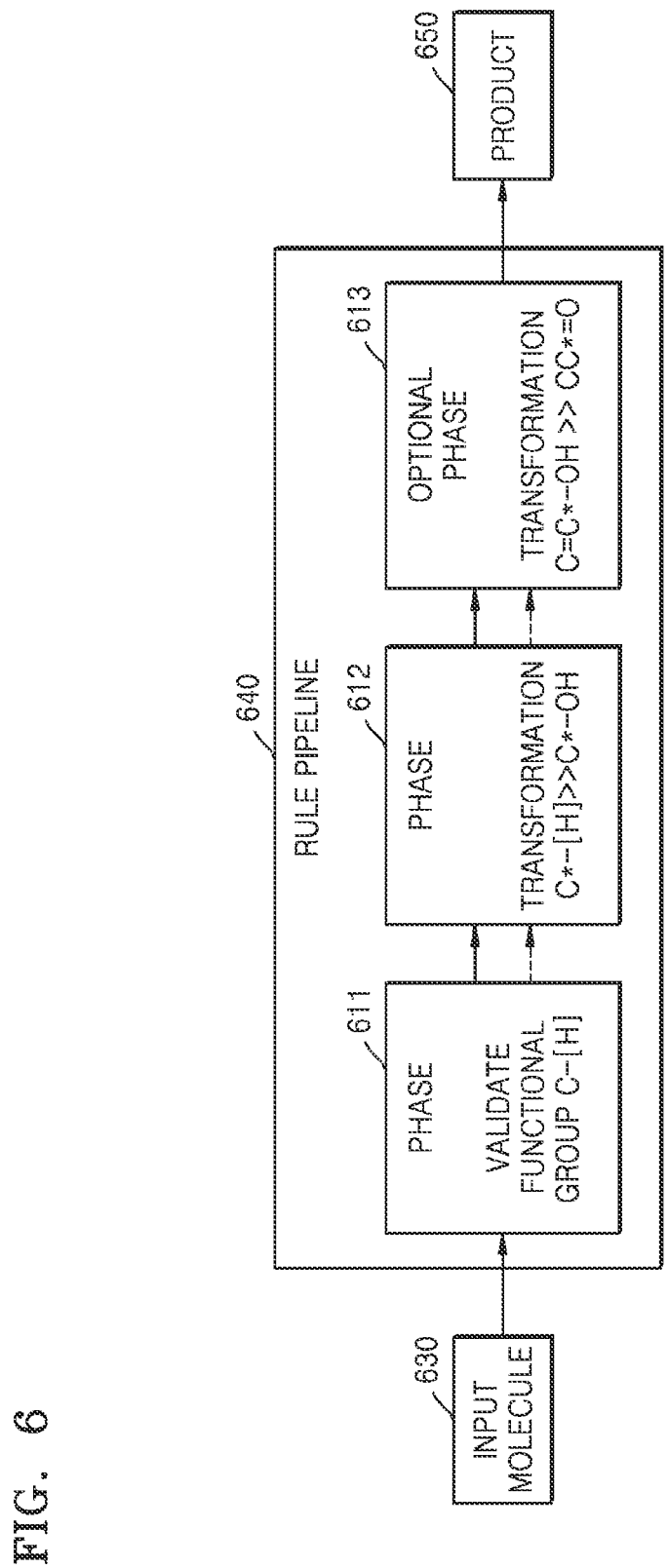
FIG. 6 illustrates a rule pipeline according to another embodiment.

FIG. 6 illustrates a rule pipeline 640 according to another exemplary embodiment.

The rule pipeline 640 of FIG. 6 includes three phases, that is, phases 611, 612, and 613. The rule pipeline 640 of FIG. 6 may be designed using the rule pipeline designing unit 120 of the in silico predicting apparatus 100.

The phase 611 is a lead phase which validates the presence of a functional group C—[H]. The phase 611 may pass, along with an output molecule, a position of an identified functional group as associated information, as illustrated by a dotted arrow in FIG. 6.

The phase 612 may transform the functional group C—[H] to C—OH based on the identified position thereof. The transformed molecule and the associated information may be forwarded to the phase 613.

The phase 613 may be designed as an optional phase. The phase 613 may transform an input molecule based on the rule C=C—OH to CC=O.

Transformation in the phase 613 is only applicable when a functional group identified in the phase 611 has =C in the neighborhood. Thus, if =C is present in the neighborhood of the functional group C=[H] of the molecule received from the phase 612, transformation in the phase 613 is applied, and otherwise, the input molecule received from the phase 612 is output as a product 650 with no modification.

According to another exemplary embodiment, the in silico predicting apparatus 100 may design the rule pipeline 140 to include configurable phases. The phase may forward an input as an output without any processing. A setting with respect to configuration may be provided as a portion of an output by a user based on associated information, and may be used by the user to change an operation of the rule pipeline 140.

According to another exemplary embodiment, the in silico predicting apparatus 100 may design a rule pipeline as a directed graph. The rule pipeline designed as a directed graph will be referred to as a 'rule directed graph' below. A phase of a rule directed graph may receive an input molecule from one or more previous phases and forward the same to one or more subsequent phases. Also, the rule directed graph may receive associated information from one or more previous phases and forward the same to one or more subsequent phases.

Phases of the rule directed graph may be grouped into one or more stages, such that all phases in a stage receives an input from the one or more phases that are grouped in a preceding stage. All of the phases that receive an inputs from the phases grouped in a previous stage are grouped in one stage. This arrangement may ensure independence of processing of all phases in a stage, and any further stage is dependent upon successful processing of the previous stages. A lead stage includes all the phases that receive a user input. The phases in a terminal stage, which are arranged as the last phases, may provide an output of the rule directed graph.

Figure 7:
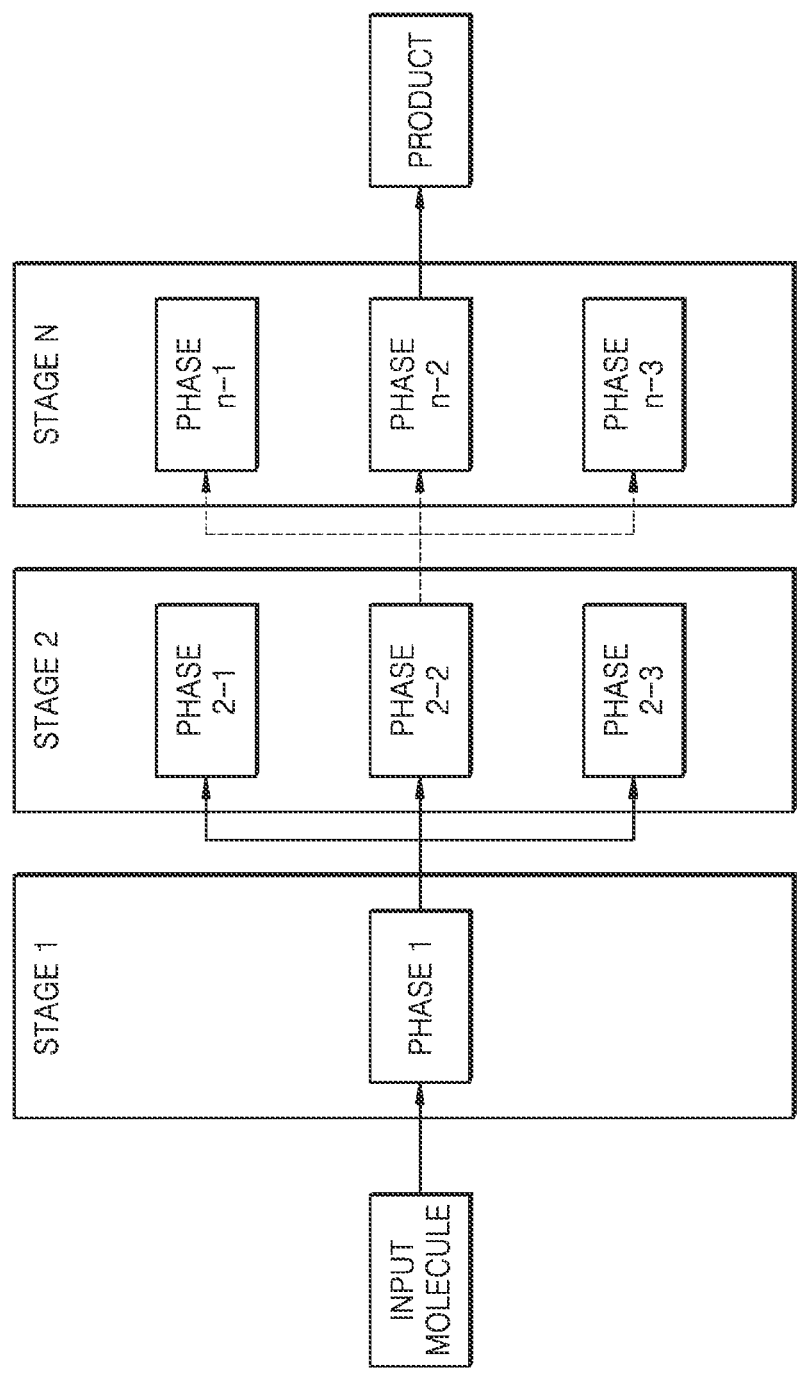
FIG. 7 illustrates a rule pipeline designed as a rule directed graph, according to an embodiment.

FIG. 7 illustrates a rule pipeline designed as a rule directed graph, according to an embodiment.

Figure 8:
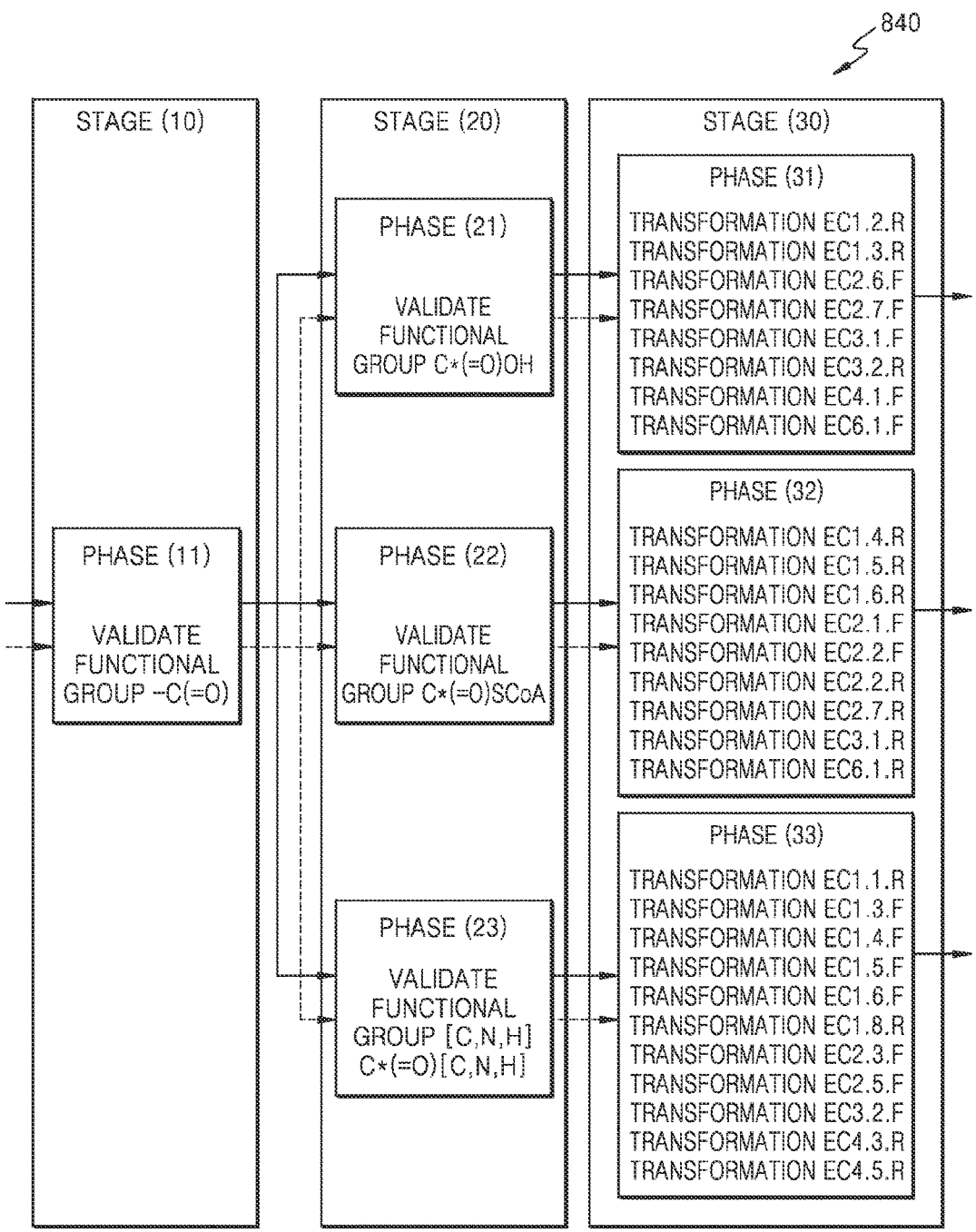
FIG. 8 illustrates a rule pipeline designed as a rule directed graph, according to an embodiment.

FIG. 8 illustrates a rule pipeline 840 designed as a rule directed graph, according to an embodiment. The rule pipeline 840 may be constructed using the in silico predicting apparatus 100 based on the rules listed in Table 1 and similarity of functional groups. A flow of molecules is denoted by a solid arrow, and a flow of associated information is denoted by a dotted arrow.

A stage 10 may include a phase 11 having a rule to validate the presence of a functional group —C=O in an input molecule. An output molecule and associated information of the phase 11 may be forwarded as an input to a stage 20. The associated information may include a position of the functional group identified in the phase 11 (—C=O).

The stage 20 may include a phase 21, a phase 22, and a phase 23, and each phase may identify the presence of —C(=O)OH, —C(=O)SCoA, and [C,N,H]C(=O)[C,N,H], respectively. The phases 21, 22, and 23 may forward the processed molecules and associated information to the respective phases 31, 32 and 33 in a stage 30.

The stage 30 may include three phases, that is, a phase 31, a phase 32, and a phase 33, each having a set of transformation rules that are specific to a predetermined functional group validated in a previous phase leading to the phase. A rule directed graph may reduce redundant computations.

A phase in a rule directed graph may receive inputs from multiple phases and process the same either independently or cumulatively. When processing the inputs independently, all rules in the phase are independently applied to the inputs received from other phases.

Figure 9A:
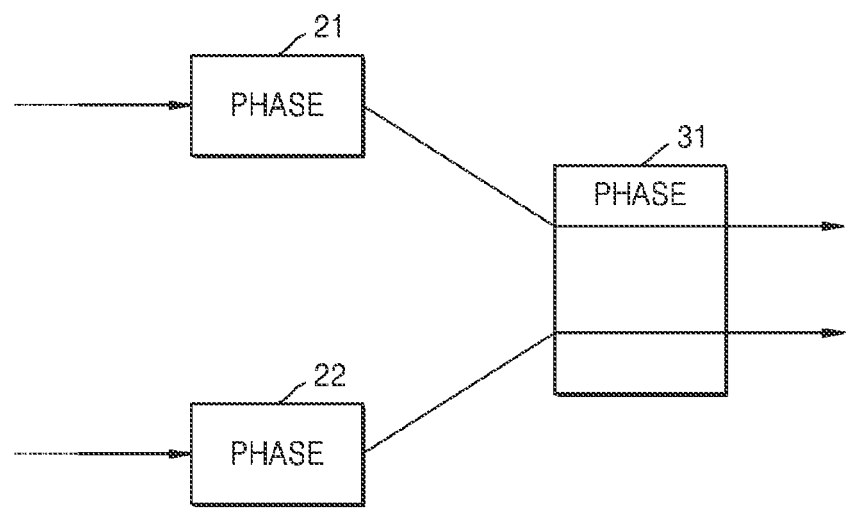
FIG. 9A illustrates independent processing of multiple inputs, performed by a phase in a rule pipeline, according to an exemplary embodiment.

FIG. 9A illustrates independent processing of inputs, performed by a phase in a rule pipeline, according to an exemplary embodiment. A scenario of FIG. 9A is equivalent to independent processing by using multiple copies of the phase 31.

Figure 9B:
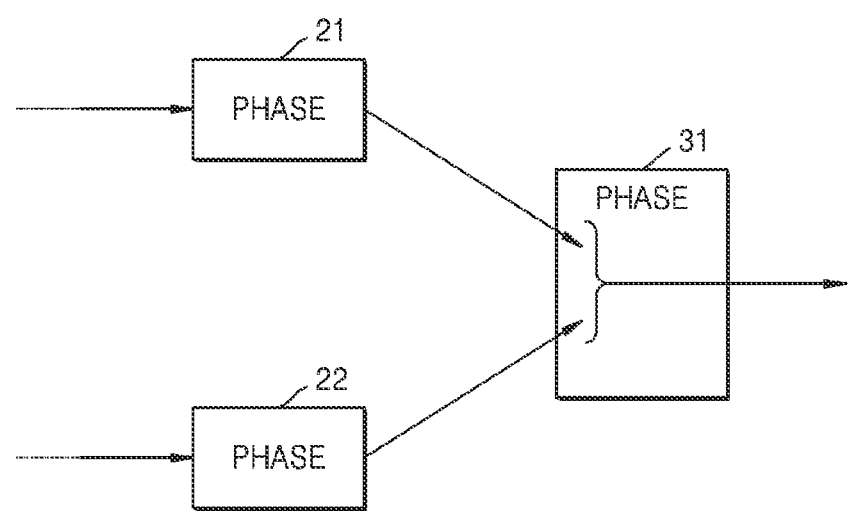
FIG. 9B illustrates cumulative processing of multiple inputs, performed by a phase in a rule pipeline, according to an exemplary embodiment.

FIG. 9B illustrates cumulative processing of inputs, performed by a phase in a rule pipeline, according to an exemplary embodiment.

For cumulative processing of inputs, the phase may process input molecules coming from previous multiple phases together. The molecules coming from various phases are considered as multiple substrates required by a rule in a phase that enacts transformation. The phase 31 may sequentially pair or combine multiple inputs received from the phase 21 and the phase 22 to process the same.

According to another exemplary embodiment, phases of a rule pipeline may be designed as metaphases. In this scenario, phases may be designed to have rule pipelines arranged parallel to each other. According to another exemplary embodiment, the phases may further include extracted rules in addition to the rule pipelines.

Figure 10:
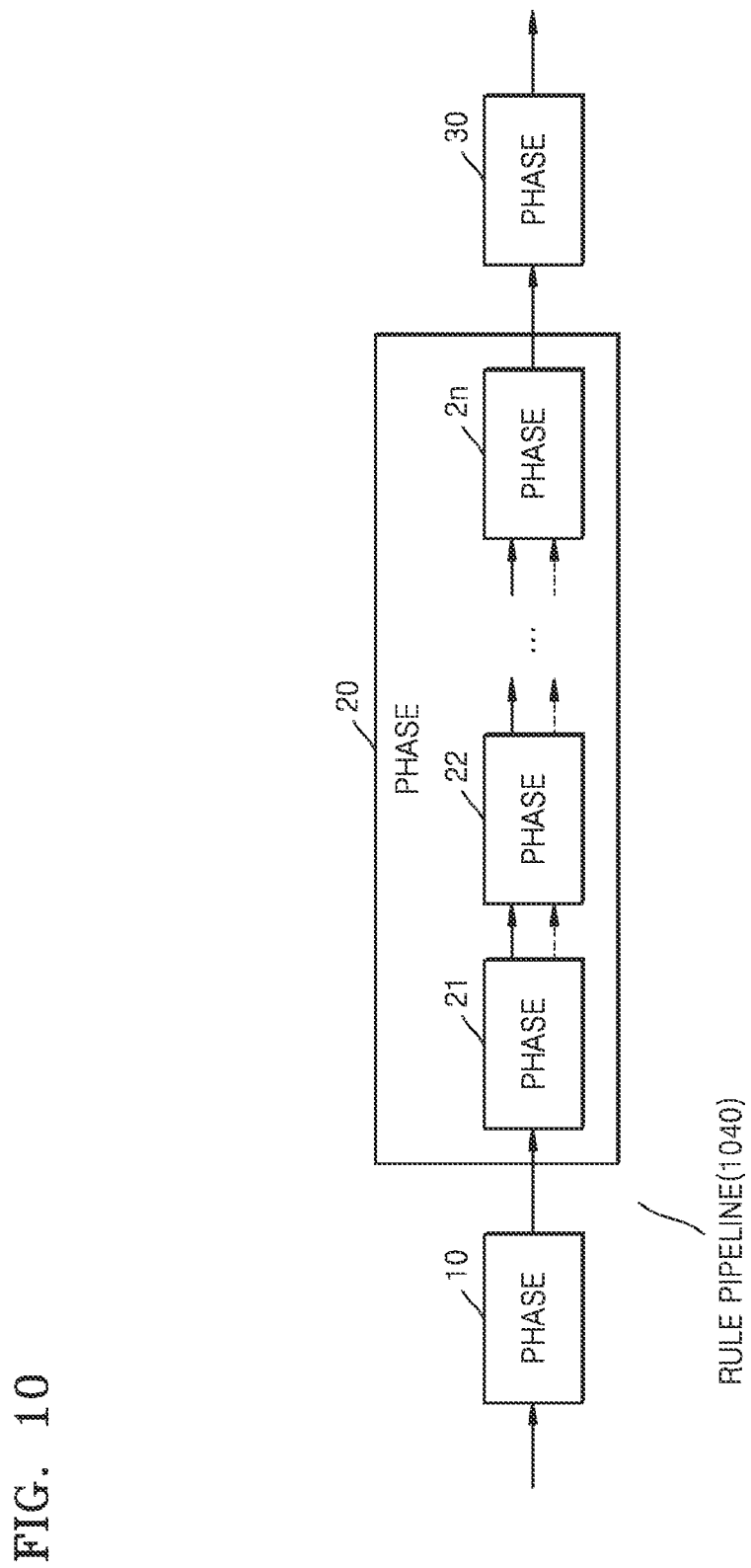
FIG. 10 illustrates a metaphase in a rule pipeline, according to an exemplary embodiment.

FIG. 10 illustrates a metaphase in a rule pipeline 1040, according to an exemplary embodiment.

The rule pipeline 1040 of FIG. 10 may include three phases 10, 20, and 30. The phase 20 is a metaphase including a rule pipeline formed of n phases 21, 22, ..., 2n. The phase 20 may include one or more rule pipelines and/or one or more rules.

The above iterative arrangement may give flexibility to a design of a complicated rule pipeline to achieve a desired output. Compared to a typical phase, a metaphase may perform either validation or transformation or a combination thereof depending upon rules and rule pipelines that are present in the phase.

The rules and the rule pipelines included in a metaphase according to an exemplary embodiment may be arranged parallel to each other, and inputs of the metaphase may be independently processed from one another through each of the rules and the rule pipelines.

Two or more rule pipelines or rules and rule pipelines in a metaphase may be connected via logical operators.

A reaction rule pipeline may be designed based on the rules for chemical conversion as listed in Table 1 (below). The schema of the rule pipelines may use a functional group as the physiochemical attributes to process and group the rules for chemical conversion.

The schema may be used to construct a chemical fingerprint of reactant patterns (e.g., reactant functional group) in order to process the rules of chemical conversion. For example, for a reactant pattern presented as SMARTS, all possible patterns may be enumerated to construct fingerprints. Fingerprints derived from various rules are compared with one another and common bits of the fingerprints are grouped. Within a group, the rules for chemical conversion with higher bit similarity may be further sub-grouped.

According to an embodiment, the rules in Table 1 may be grouped based on a similarity of a functional group that is transformed through a reaction process (at Level 1). The rules for chemical conversion may be further sub-grouped based on matches of functional groups (at Level 0). Each group may then be converted to a rule pipeline or a rule graph. A process of converting groups of rules for chemical conversion to pipelines is illustrated in FIGS. 5 and 8.

Table 1 below shows a sample reaction rule library according to an embodiment (Yim et al, Nature Chemical Biology 7, 445-452 (2011)). Each chemical rule is split into forward and reverse components, and may be classified by designating rule IDs thereof as F (forward) and R (reverse). Except for one case, both forward and reverse rules are equivalent. The rules may be grouped based on similarity of functional groups involved in a reaction process, and the groups may be used to design a rule pipeline.

TABLE 1

| Rule ID | Reaction Rule | Functional Group | Level 0 | Level 1 |
|---|---|---|---|---|
| EC1.7.R | [H,C,O:6]—[C:1](—[H,C:3])=[C:2](—[H,C:4])—[H,C,N,O:5]>>[H,C,O:6]—[C:1](—[H,C:3])—[C:2](—[H,C:4])—[H,C,N,O:5] | C=C | C=C | C=C |
| EC4.2.R | [C:1](—[C,H:3])(—[C,H:4])=[C:2](—[C,H:5])—[C,H:6]>>[C:1](—[C,H:3])(—[C,H:4])—[C:2](—[C,H:5])(—[C,H:6])—[O] | C=C | | |
| EC4.4.R | [C:1](—[C,H:3])(—[C,H:4])=[C:2](—[C,H:5])—[C,H:6]>>[C:1](—[C,H:3])(—[C,H:4])—[C:2](—[C,H:5])(—[C,H:6])—[N] | C=C | | |
| EC1.2.R | [C:3]—[C;X3:1](=[O:2])—[O:4]—[H:5]>>[C:3]—[C:1](—[O:2]) | C(=O)OH | C(=O)OH | C=O |
| EC1.3.R | [C:3]—[C;X3:1](=[O:2])—[O:4]—[H:5]>>[C:3]—[C:1](=[O:2]) | C(=O)OH | | |
| EC2.6.F | [C;X3:1](=[O:2])—[O:4]—[H:5]>>[C;X3:1](=[O:2])—[O:4]—P(O)(O)=O | C(=O)OH | | |
| EC2.7.F | [C,H:3]—[C:1](=[O:2])—[O:4]—[H:5]>>[C,H:3]—[C:1](=[O:2])—S[CoA] | C(=O)OH | | |
| EC3.1.F | [C,H:3]—[C:1](=[O:2])—[O:4]—[H:5]>>[C,H:3]—[C:1](=[O:2])—S[CoA] | C(=O)OH | | |
| EC3.2.R | [H]—O[C;X3:1](=[O:8])[C:2][C:3][C:4][C:5][C:6][N:7](—[H])—[H]>>[C;X3:1]1(=[O:8])[C:2][C:3][C:4][C:5][C:6][N:7]1 | C(=O)OH | | |
| EC4.1.F | [C:4]—[C;X3:1](=[O:2])—[O:3]—[H]>>[C:4] | CC(=O)OH | | |
| EC6.1.F | [C,H:3]—[C:1](=[O:2])—[O:4]—[H:5]>>[C,H:3]—[C:1](=[O:2])—S[CoA] | C(=O)OH | | |
| EC1.4.R | [C,H:3]—[C:1](=[O:2])—[S:4]—[CoA:5]>>[C,H:3]—[C:1](=[O:2]) | C(=O)S[CoA] | C(=O)S[CoA] | |
| EC1.5.R | [C:3]—[C;X3:1](=[O:2])—S—[CoA]>>[C:3]—[C:1](=[O:2])—[C:4](=[O:5])—[O:6] | C(=O)S[CoA] | | |
| EC1.6.R | [H:4]—[C:3]—[C;X3:1](=[O:2])—[S:5][CoA:6]>>[C;X3:1](=[O:2])—[C:3]—[C:7](=[O:8])—[O:9] | C(=O)S[CoA] | | |
| EC2.1.F | [C,H:3]—[C:1](=[O:2])—[S:4]—[CoA:5]>>[C,H:3]—[C:1](=[O:2])—O—P(O)(O)=O | C(=O)S[CoA] | | |
| EC2.2.F | [C,H:3]—[C:1](=[O:2])—[S:4]—[CoA:5]>>[C,H:3]—[C:1](=[O:2])—[C:6]—[C:7](=[O:8])—[S:4]—[CoA:5] | C(=O)S[CoA] | | |
| EC2.2.R | [C,H:3]—[C:1](=[O:2])—[C:6](—[H:9])(—[H:10])—[C:7](=[O:8])—[S:4]—[CoA:5]>>[C,H:3]—[C:1](=[O:2])—[S:4]—[CoA:5] | C(=O)S[CoA] | | |
| EC2.7.R | [C,H:3]—[C:1](=[O:2])—[S:5][CoA:6]>>[C,H:3]—[C:1](=[O:2])—[O:4] | C(=O)S[CoA] | | |

TABLE 1-continued

| Rule ID | Reaction Rule | Functional Group | Level 0 | Level 1 |
|---|---|---|---|---|
| EC3.1.R | [C,H:3]—[C:1](=[O:2])—[S:5][CoA:6]>>[C,H:3]—[C:1](=[O:2])—[O:4] | C(=O)S[CoA] | | |
| EC6.1.R | [C,H:3]—[C:1](=[O:2])—[S:5][CoA:6]>>[C,H:3]—[C:1](=[O:2])—[O:4] | C(=O)S[CoA] | | |
| EC1.1.R | [H,C:3]—[C:1](=[O:2])—[C,H:4]>>[H,C:3]—[C:1](—[O:2])—[C,H:4] | C=O | C=O | |
| EC1.3.F | [C:3]—[C;X3:1](=[O:2])—[H:4]>>[C:3]—[C:1](=[O:2])—O | C=O | | |
| EC1.4.F | [C:3]—[C;X3:1](=[O:2])—[H:4]>>[C:3]—[C:1](=[O:2])—S[CoA] | C=O | | |
| EC1.5.F | [C:3]—[C;X3:1](=[O:2])—[C:4](=[O:5])—[O:6]—[H:7]>>[C:3]—[C:1](=[O:2])—S[CoA] | C=O | | |
| EC1.6.F | [H:8]—[C;X3:1](=[O:2])—[C:3]—[C:4](=[O:5])—[O:6]—[H:7]>>[C:3]—[C:1](=[O:2])—S[CoA] | C=O | | |
| EC1.8.R | [H,C:3]—[C:1](=[O:8])—[C,H:2]>>[H,C:3]—[C:1](—[N:4])—[C,H:2] | C=O | | |
| EC2.3.F | [H,C:3]—[C:1](=[O:8])—[C,H:2]>>[H,C:3]—[C:1](—[N:4])—[C,H:2] | C=O | | |
| EC2.5.F | [H,C:3]—[C:1](—[H])(—[H])—[C:2](=[O:4])—[C:5](=[O:6])—[O:7]—[H]>>[H,C:3]—[C:1](—[H])=[C:2](—[O:4]—P(O)(O)=O)—[C:5](=[O:6])—[O:7] | CC(=O) | | |
| EC3.2.F | [C;X3:1]1(=[O:8])[C:2][C:3][C:4][C:5][C:6][N:7](—[H])1>>O[C;X3:1](=[O:8])[C:2][C:3][C:4][C:5][C:6][N:7] | C(=O)@N | | |
| EC4.3.R | [C:1](=[O:3])(—[C,H:4])—[C:2](—[C,H:5])(—[C,H:6])—[H]>>[C:1](—[O:3])(—[C,H:4])—[C:2](—[C,H:5])(—[C,H:6])—[O] | CC(=O) | | |
| EC4.5.R | [H]—[C:1](—[C,H:4])(—[H])—[C:2](—[C,H:5])(=[O:3])>>[H]—[C:1](—[O:3])(—[C,H:4])—[C:2](—[C,H:5])—[N] | CC(=O) | | |
| EC5.2.F | [O,S:5]—[C:1](=[O:6])—[C:3](—[C:4])(—[H])—[C:2](—[H])(—[H])—[H]>>[O,S:5]—[C:1](=[O:6])—[C:2](—[C:3](—[C:4]) | C(C)C | CCC | CCC |
| EC5.2.R | [O,S:5]—[C:1](=[O:6])—[C:2](—[H])(—[H])—[C:3](—[C:4])(—[H])—[H]>>[O,S:5]—[O:1](=[O:6])—[C:3](—[C:4])(—[C:2](—[H])(—[H])—[H] | CCC | | |
| EC1.7.F | [H,C,O:2]—[C:1](—[H:6])(—[H,C:3])—[C:2](—[H:7])—[H,C:4])—[H,C,N,O:5]>>[H,C,O:2]—[C:1](—[H,C:3])=[C:2](—[H,C:4])—[H,C,N,O:5] | HC—CH | C—H | C—H |
| EC4.1.R | [C;!H0:4]—[H]>>[C:4]—[C;X3:1](=[O:2])—[O:3] | C—H | | |
| EC1.8.F | [H,C:3]—[C:1](—[N:4])—[H:5])(—[H:6])(—[H:7])—[C,H:2]>>[H,C:3]—[C:1](=[O:8])—[C,H:2] | C—NH2 | CNH2 | C—NH2 |
| EC2.3.R | [H,C:3]—[C:1](—[N:4])—[H:5])(—[H:6])(—[H:7])—[C,H:2]>>[H,C:3]—[C:1](=[O:8])—[C,H:2] | C—NH2 | | |
| EC4.4.F | [H]—[C:1](—[C,H:3])(—[C,H:4])—[C:2](—[C,H:5])(—[C,H:6])—[N](—[H])—[H]>>[C:1](—[C,H:3])(—[C,H:4])=[C:2](—[C,H:5])—[C,H:6] | CC(NH2) | | |
| EC5.1.F | [H]—[C:1](—[N:3](—[H])—[H])(—[C,H:4])—[C:2](—[C,H:5])(—[H])—[H]>>[H]—[C:1](—[C,H:4])(—[H])—[C:2](—[C,H:5])(—[N:3](—[H])—[H])—[H] | CCNH2 | | |
| EC1.1.F | [H,C:3]—[C:1](—[O:2]—[H:5])(—[H:6])—[C,H:4]>>[H,C:3]—[C:1](=[O:2])—[C,H:4] | C—OH | C—OH | C—O |
| EC1.2.F | [C:3]—[C;X4:1]—[O:2]—[H:5])(—[H:6])—[H:4]>>[C:3]—[C:1](=[O:2])—O | C—OH | | |
| EC2.4.F | [H,C:3]—[C:1](—[O:2]—[H:5])(—[C,H:6])—[C,H:4]>>[H,C:3]—[C:1](—[O:2]—P(O)(O)=O)—(—[C,H:6])—[C,H:4] | C—OH | | |
| EC4.2.F | [H]—[C:1](—[C,H:3])(—[C,H:4])—[C:2](—[C,H:5])(—[C,H:6])—[O]—[H]>>[C:1](—[C,H:3])(—[C,H:4])=[C:2](—[C,H:5])—[C,H:6] | CC(OH) | | |

TABLE 1-continued

| Rule ID | Reaction Rule | Functional Group | Level 0 | Level 1 |
|---|---|---|---|---|
| EC4.3.F | [H]—[C:1](—[O:3]—[H])(—[C,H:4])—[C:2](—[C,H:5])(—[C,H:6])—[O]—[H]>>[C:1](=[O:3])(—[C,H:4])—[C:2](—[C,H:5])—[C,H:6] | CC(OH) | | |
| EC4.5.F | [H]—[C:1](—[O:3]—[H])(—[C,H:4])—[C:2](—[C,H:5])(—[H])—[N](—[H])—[H]>>[C:1](—[C,H:4])—[C:2](—[C,H:5])(=[O:3]) | CC(OH) | | |
| EC2.1.R | [C,H:3]—[C:1](=[O:2])—O—P(O—[H])(O—[H])=O>>[C,H:3]—[C:1](=[O:2])—[S:4]—[CoA:5] | C(=O)OPO3 | COPO3 | |
| EC2.4.R | [H,C:3]—[C:1](—[O:2])—P(O—[H])(O—[H])=O)(—[C,H:6])—[C,H:4]>>[H,C:3]—[C:1](—[O:2])(—[C,H:6])—[C,H:4] | C—OPO3 | | |
| EC2.5.R | [H,C:3]—[C:1](—[H])=[C:2](—[O:4]—P(O—[H])(O—[H])=O)—[C:5](=[O:6])—[O:7]—[H]>>[H,C:3]—[C:1](—[H])—[C:2](=[O:4])—[C:5](=[O:6])—[O:7] | C=COPO3 | | |
| EC2.6.R | [C;X3:1](=[O:2])—[O:4]—P(O—[H])(O—[H])=O>>[C;X3:1](=[O:2])—[O:4]—[H:5] | C(=O)OPO3 | | |

A method of processing rule pipelines for predicting chemical reactions for an input molecule will be described based on the rule pipelines described with reference to FIGS. 2 through 10.

Figure 11:
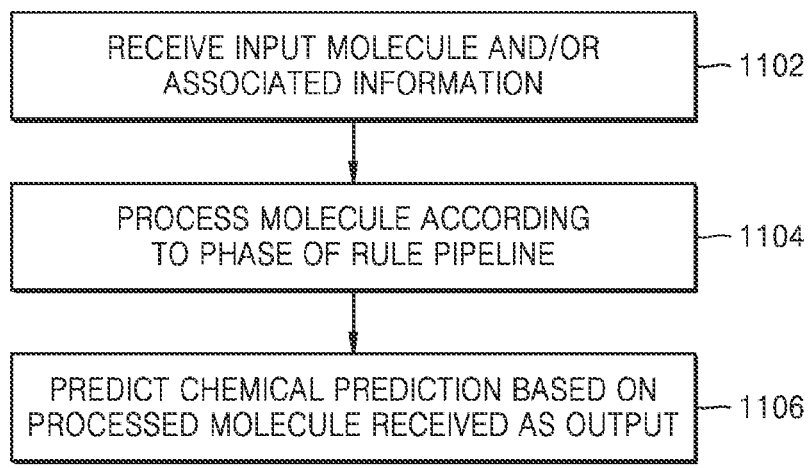
FIG. 11 is flowchart illustrating a method of processing a rule pipeline by using an in silico predicting apparatus according to an exemplary embodiment.

FIG. 11 is flowchart illustrating a method of processing a rule pipeline by using an in silico predicting apparatus according to an exemplary embodiment.

FIG. 11 is directed to a method of processing the designed rule pipeline described above with reference to FIGS. 2 through 10, and thus, details about the rule pipeline 140 described above but omitted here also apply to the method of processing a rule pipeline according to the exemplary embodiment of FIG. 11.

In operation 1102, an input molecule and/or associated information may be received. An input molecule may be represented using one of the standard molecular representations, and atoms in the molecule may be represented as either native elements or derived atom types. The associated information may be provided as an input based on the design of a rule pipeline being processed.

In operation 1104, the molecule received in operation 1102 may be processed according to phases of the rule pipeline. The input molecule may be sequentially processed through each phase of the rule pipeline and associated information that is generated with the processed input molecule may be fed as an input to a subsequent phase. The processed molecule may be selected as an output of the rule pipeline. Also, processing of the rule pipeline may be terminated when the phase fails to generate an output molecule.

In operation 1106, the molecule received as the output of the processing of the rule pipeline may be used to predict chemical reactions. The output of the processing of the rule pipeline may refer to an output from a terminal phase arranged as a last phase from among one or more phases of the rule pipeline or any other phase that is selected differently from the terminal phase. The output molecule may be paired with the input molecule based on the schema of the rule pipeline and the represented transformation to predict reactions. According to an embodiment, a reaction may be predicted for each set of molecules in the output of the processing of the rule pipeline, wherein, the input molecule may be considered as a reactant and the corresponding output molecule may be considered as a product.

Each phase of the rule pipeline may perform validation or transformation on an input molecule by applying the extracted rules and/or the rule pipelines in the phase. Associated information may selectively used for the processing of the molecules. Nested rule pipelines in the metaphase may also be processed in the same manner as described with reference to FIG. 10.

While processing the input molecule through a phase, all the rules and/or rule pipelines that are present in the phase may be applied on the input molecule sequentially or in parallel, to produce an output.

While processing a phase designed for validation, molecules received as an input may be processed as per the phase, and subsequent to successful validation the input molecules, with no modifications, may be produced as an output. Similarly, while processing a phase designed for transformation, molecules received as an input may be processed and transformed as per the phase and transformed molecules may be produced as an output.

A phase that generates received associated information as an output without any change may not provide the output to a subsequent phase. According to another embodiment, the associated information may be generated or modified. Associated information may be modified by adding, deleting, overwriting or combination of these according to processing performed in the phase.

As described earlier, the associated information received by the lead phase or processed associated information received by a current phase from a previous phase may play an important role in overall processing. Based on the associated information received from the previous phase and the design of the rule pipeline, the rules and/or the rule pipelines in the phase may process atoms of the molecules of the input that were processed in the previous phase.

Subsequent phases of the rule pipeline are restricted to atoms that were processed and validated by one of the previous phases of the rule pipeline. This also enables the rule pipeline to reuse computations. Further, based on the associated information received from the previous phase and the design of the rule pipeline, a phase may omit from processing the atoms of the input molecules that were processed in the previous phase.

Apart from the above-described scenarios, the processing of the rule pipeline may also be governed by certain specific phases designed to be processed according to a user configuration. The configuration settings may be provided by the user as associated information along with the input. During the processing of the rule pipeline, phases configured by the user in the rule pipeline may be processed based on received configuration settings, such that a current phase is instructed through the configuration settings, and an input to the current phase may be produced as an output without any processing.

In another scenario of the processing of the rule pipeline, some phases of the rule pipeline may be designated as optional, such that an input to the optional phase is produced as an output if the input to the optional phase fails to produce an output. Accordingly, flexibility of carrying forward the processing of the rule pipeline may be provided compared to a default termination of the processing of the rule pipeline in the event of a phase failing to produce an output.

A rule pipeline for processing according to an embodiment may be designed as a rule directed graph. A phase of a directed graph may receive an input from one or more other phases, and a phase may feed an output to the one or more phases.

The input molecules may be processed according to a phase of the rule directed graph. The input molecules may be sequentially processed through each stage, such that phases grouped in a stage are processed before proceeding to a next stage. An output of a phase and associated information may be fed to subsequent phases. The processed molecules produced as an output from a terminal stage or selected phases of the rule directed graph or combination of both phases (combination of the terminal stage and selected phase) may be selected as outputs of the processing of the rule pipeline designed as the rule directed graph. Furthermore, the processing may be terminated if all the phases in a stage fail to generate an output.

When processing of the molecules received as inputs from multiple phases, the rules in the phase of the rule directed graph may process the inputs independently or cumulatively as described above.

Figure 12:
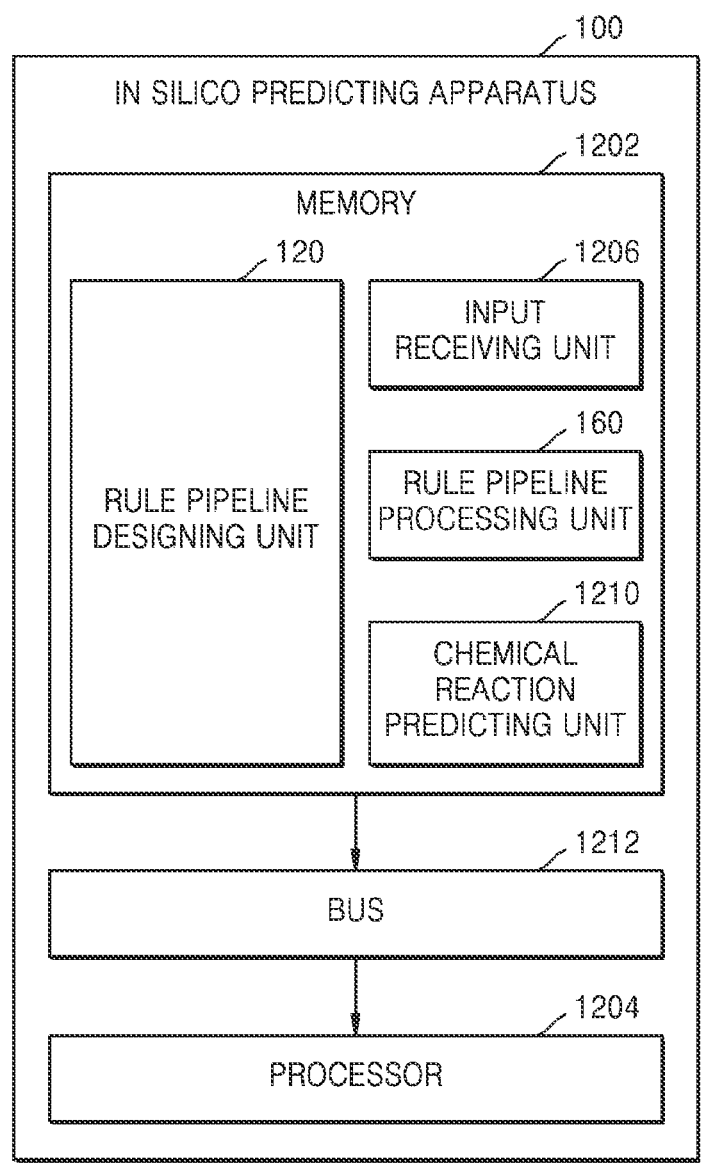
FIG. 12 is a block level diagram illustrating an in silico predicting apparatus according to an exemplary embodiment.

FIG. 12 is a block level diagram illustrating an in silico predicting apparatus 100 according to an exemplary embodiment.

The in silico predicting apparatus 100 may be configured to design a rule pipeline to predict chemical reactions for molecules received as a user input, and may selectively use associated information.

The in silico predicting apparatus 100 according to an embodiment may include a processor 1204 and a memory 1202 that is coupled to the processor 1204 via a bus 1212.

Examples of the processor 1204 may include, but not limited to, a microprocessor, a microcontroller, a complex instruction set computing microprocessor (CISC), a reduced instruction set computing microprocessor (RISC), a very long instruction word (VLIW) microprocessor, an explicitly parallel instruction computing microprocessor (EPIC), a digital signal processor, and any other type of processing circuit, or a combination thereof.

The memory 1202 may include a plurality of software modules or units that are stored in the form of an executable program that instructs the processor 1204 to perform the operations described with reference to FIGS. 2 through 11. The memory 1202 may include a rule pipeline designing unit 120, an input receiving unit 1206, a rule pipeline processing unit 160, and a chemical reaction prediction unit 1210.

Examples of a computer memory element may include any suitable non-transitory memory devices for storing data and executable programs, such as a read only memory (ROM), a random access memory (RAM), an erasable programmable read only memory (EPROM), an electrically erasable programmable read only memory (EEPROM), a hard drive, and a memory card. The in silico predicting apparatus 100 according to an embodiment may be implemented in conjunction with program modules, including functions, procedures, data structures, and application programs for performing tasks or defining abstract data types or low-level hardware contexts.

The rule pipeline designing unit 120 may instruct the processor 1204 to perform the methods illustrated in the flowcharts of FIGS. 2 and 3.

The input receiving module 1206 may instruct the processor 1204 to perform operation 1102 of FIG. 11.

The rule pipeline processing module 1208 may instruct the processor 1204 to perform operation 1104 of FIG. 11.

The chemical reaction prediction module 1210 may instruct the processor 1204 to perform operation 1106 of FIG. 11.

While the inventive concept has been particularly shown and described with reference to exemplary embodiments thereof, it will be obvious to those of ordinary skill in the art that various substitutes, changes, and modifications in form and details may be made therein without departing from the spirit and scope of the inventive concept as defined by the following claims. Thus, all details described in the present specification with reference to the exemplary embodiments and drawings should be interpreted as being exemplary and non-limiting.

The device described herein may include a processor, a memory for storing program data and executing it, a permanent storage such as a disk drive, a communications port for handling communications with external devices, and user interface devices, including a display, keys, etc. When software modules are involved, these software modules may be stored as program instructions or computer readable codes executable on the processor on a computer-readable media such as read-only memory (ROM), random-access memory (RAM), CD-ROMs, magnetic tapes, floppy disks, and optical data storage devices. The computer readable recording medium can also be distributed over network coupled computer systems so that the computer readable code is stored and executed in a distributed fashion. This media can be read by the computer, stored in the memory, and executed by the processor.

The inventive concept may be described in terms of functional block components and various processing steps. Such functional blocks may be realized by any number of hardware and/or software components configured to perform the specified functions. For example, the inventive concept may employ various integrated circuit components, e.g., memory elements, processing elements, logic elements, look-up tables, and the like, which may carry out a variety of functions under the control of one or more microprocessors or other control devices. Similarly, where the elements of the inventive concept are implemented using software programming or software elements the inventive concept may be implemented with any programming or scripting language such as C, C++, Java, assembler, or the like, with the various algorithms being implemented with any combination of data structures, objects, processes, routines or other programming elements. Functional aspects may be implemented in algorithms that execute on one or more processors. Furthermore, the inventive concept could employ any number of conventional techniques for electronics configuration, signal processing and/or control, data processing and the like. The words "mechanism" and "element" are used broadly and are not limited to mechanical or physical embodiments, but can include software routines in conjunction with processors, etc.

The particular implementations shown and described herein are illustrative examples of the inventive concept and are not intended to otherwise limit the scope of the inventive concept in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

The use of the terms "a" and "an" and "the" and similar referents in the context of describing the inventive concept (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Finally, the steps of all methods described herein can be performed in any suitable order unless otherwise indicated herein or otherwise clearly contradicted by context. The use of any and all examples, or exemplary language (e.g., "such as") provided herein, is intended merely to better illuminate the inventive concept and does not pose a limitation on the scope of the inventive concept unless otherwise claimed. Numerous modifications and adaptations will be readily apparent to those skilled in this art without departing from the spirit and scope of the inventive concept.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method for in silico prediction of chemical reactions, the method comprising:
    designing, by at least one processor of an in silico prediction apparatus, a rule pipeline;
    processing, by the at least one processor, at least one input molecule using the designed rule pipeline; and
    predicting, by the at least one processor, a chemical reaction based on the at least one processed input molecule,
    wherein the designed rule pipeline includes an arrangement of a plurality of phases including at least one rule for chemical conversion, and wherein in the designing of the rule pipeline, each phase of the plurality of phases is designed to perform one of validation and transformation based on a rule included in the each phase,
    wherein the designing of the rule pipeline further comprises designing at least one phase as an optional phase, and
    wherein, if the optional phase fails to produce an output from a received input, the optional phase generates the received input as an output with no modification.

2. The method of claim 1, wherein the designing of the rule pipeline comprises:
    processing the at least one rule for chemical conversion based on at least one physiochemical attribute defined in a schema;
    grouping the processed at least one rule for chemical conversion into at least one group; and
    designing the rule pipeline for each of the at least one group.

3. The method of claim 2, wherein the designing of the rule pipeline for each of the at least one group comprises:
    processing the plurality of rules of the one group to extract at least one rule; and
    arranging the at least one extracted rule,
    wherein the arranging of the at least one extracted rule comprises arranging the at least one phase including the at least one extracted rule, and
    in the arranging of the at least one phase, the at least one phase is arranged such that at least one output of a phase is fed as at least one input of a subsequent phase.

4. The method of claim 3, wherein the designing of the rule pipeline for each of the at least one group further comprises connecting a plurality of extracted rules to one another via a logical operator.

5. The method of claim 3, wherein each of the at least one extracted rule is one of a validation rule and a transformation rule.

6. The method of claim 1, wherein in the designing of the rule pipeline, a lead phase arranged as a lead phase of the rule pipeline receives the at least one input molecule while a terminal phase arranged as a last phase generates the at least one processed molecule as an output.

7. The method of claim 1, wherein the designing of the rule pipeline comprises designing at least one phase for receiving, generating, or modifying associated information, and
    the associated information comprises an atom of a molecule that is received as an input by a phase and is processed in a previous phase, an atom of at least one molecule that is eligible for processing in the phase, a result of at least one computation performed previously, at least one user parameter, and at least one user configuration,
    wherein the generating or modifying of the associated information is performed by at least one of adding, deleting, and overwriting the associated information.

8. The method of claim 7, wherein in the designing of the rule pipeline, the at least one rule pipeline is designed such that one of validation or transformation of the input molecule is performed based on the associated information in each of the at least one phase.

9. The method of claim 7, wherein in the designing of the rule pipeline, a phase is designed to omit processing of at least atom with respect to at least one molecule received as an input by at least one phase, and information about the at least one atom for which the processing is omitted is included in the associated information.

10. The method of claim 1, wherein the designing of the rule pipeline comprises designing at least one phase as a metaphase including at least one rule pipeline, and
    the metaphase comprises at least one rule pipeline, and if the metaphase comprises at least two rule pipelines, the rule pipelines are arranged in parallel.

11. The method of claim 10, in the designing of the rule pipeline, the metaphase is designed such that the at least one input molecule is validated or transformed.

12. The method of claim 1, wherein in the designing of the rule pipeline, the designing of the rule pipeline is performed via a directed graph,
   wherein the at least one phase receives at least one input from at least one previous phase and forwards the at least one output to at least one subsequent phase.

13. The method of claim 12, wherein the designing of the rule pipeline comprises grouping the plurality of phases into at least one stage,
   wherein a terminal phase arranged as a last phase generates the at least one processed molecule as an output, and a lead phase arranged as a lead phase receives the at least one input molecule.

14. The method of claim 12, wherein in the designing of the rule pipeline, the at least one rule pipeline is designed such that a plurality of rules included in a phase applies independently or cumulatively to at least one input received by the phase from a plurality of previous phases.

15. The method of claim 1, wherein the processing of the at least one input molecule via the rule pipeline comprises:
   receiving the at least one molecule as input; and
   sequentially processing the at least one input molecule according to at least one phase of the rule pipeline,
   wherein in the sequentially processing, at least one output of at least one phase from among the at least one phase is fed as an input of a subsequent phase.

16. The method of claim 1, wherein the predicting of a chemical reaction based on the at least one processed molecule comprises selecting one of the at least one phase to predict at least one chemical reaction based on the selected phase.

17. An in silico prediction apparatus, comprising:
   a memory; and
   at least one processor operatively coupled to the memory, wherein the at least one processor is configured to:
   design a rule pipeline;
   receive at least one molecule to be processed;
   process the at least one molecule according to at least one phase of the rule pipeline; and
   predict at least one chemical reaction based on at least one output according to processing based on the rule pipeline,
   wherein the at least one phase is designed to perform one of validation and transformation based on a rule included in the at least one phase, and
   wherein the at least one processor is further configured to design at least one phase as an optional phase, and
   wherein, if the optional phase fails to produce an output from a received input, the optional phase generates the received input as an output with no modification.

18. A non-transitory computer readable recording medium having embodied thereon a program for executing a method for in silico prediction of chemical reactions, wherein execution of the program by at least one processor, causes the at least one processor to:
   design a rule pipeline;
   process at least one input molecule using the designed rule pipeline; and
   predict a chemical reaction based on the at least one processed input molecule,
   wherein the designed rule pipeline includes an arrangement of a plurality of phases including at least one rule for chemical conversion, and wherein in the designing of the rule pipeline, each phase of the plurality of phases is designed to perform one of validation and transformation based on a rule included in the each phase,
   wherein the at least one processor is further configured to design at least one phase as an optional phase, and
   wherein, if the optional phase fails to produce an output from a received input, the optional phase generates the received input as an output with no modification.

* * * * *